United States Patent

Goralski et al.

[11] 3,946,007
[45] Mar. 23, 1976

[54] 1-(ARYLTHIO, ARYLSULFINYL AND ARYLSULFONYL)-1,1-DIHALOMETHANESULFONAMIDES

[75] Inventors: Christian T. Goralski; Thomas C. Klingler, both of Midland, Mich.

[73] Assignee: The Dow Chemical Company, Midland, Mich.

[22] Filed: Mar. 3, 1975

[21] Appl. No.: 554,953

Related U.S. Application Data

[63] Continuation-in-part of Ser. No. 351,070, April 13, 1973, abandoned.

[52] U.S. Cl.. 260/247.1 R; 260/293.73; 260/556 A; 424/248; 424/267; 424/321
[51] Int. Cl.² ................................ C07D 295/22
[58] Field of Search..... 260/556 A, 247.1 R, 293.73

[56] References Cited
UNITED STATES PATENTS

| | | | |
|---|---|---|---|
| 3,412,149 | 11/1968 | Schlor et al...................... | 260/556 A |
| 3,641,033 | 2/1972 | Levine........................... | 260/294.8 F |
| 3,766,172 | 10/1973 | Phillips......................... | 260/239 BF |
| 3,862,184 | 1/1975 | Goralski et al. ................ | 260/293.73 |
| 3,865,822 | 2/1975 | Goralski et al.................. | 260/247.1 R |
| 3,895,010 | 7/1975 | Goralski et al. ................ | 260/293.73 |

OTHER PUBLICATIONS
Allinger et al., Organic Chemistry (1971) p. 608.

*Primary Examiner*—Sherman D. Winters
*Attorney, Agent, or Firm*—Theodore Post; C. Kenneth Bjork

[57] ABSTRACT

The compounds of the formula

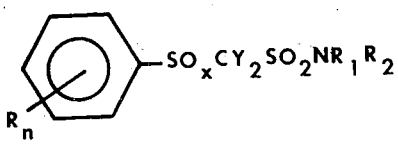

in which R is lower alkyl, lower alkoxy or halo, $x$ is an integer from 0 to 2, $n$ is an integer from 0 to 3, Y is halo and $R_1$ and $R_2$ independently are hydrogen, lower alkyl, phenyl or substituted phenyl, or, together with the nitrogen atom, form a heterocyclic ring also containing up to one oxygen atom in the heterocycle. The compounds in which $x$ is 0 are prepared by adding chlorine or bromine to a 1-arylthiomethanesulfonamide in the presence of pyridine to form the 1-arylthio-1, 1-dihalomethanesulfonamide. The compounds in which $x$ is 1 or 2 is prepared by adding sodium hypochlorite or sodium hypobromite to a 1-(arylsulfinyl)methane-sulfonamide or a 1-(arylsulfonyl)methanesulfonamide to form the 1-(arylsulfinyl)-1,1-dihalomethanesulfonamide or 1-(arylsulfonyl)-1,1-dihalomethanesulfonamide, respectively. The compounds are useful as antimicrobial agents.

11 Claims, No Drawings

1-(ARYLTHIO, ARYLSULFINYL AND ARYLSULFONYL)-1,1-DIHALOMETHANESULFONAMIDES

CROSS-REFERENCE TO RELATED APPLICATION

This application is a continuation-in-part of U.S. Pat. application Ser. No. 351,070, filed Apr. 13, 1973, now abandoned.

SUMMARY OF THE INVENTION

This invention concerns 1-arylthio-1,1-dihalomethanesulfonamides and the corresponding sulfinyl and sulfonyl derivatives corresponding to the formula

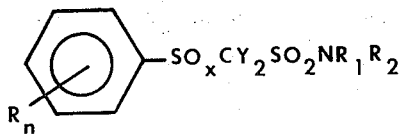

wherein R represents hydrogen, lower alkyl, lower alkoxy or halo, $x$ represents an integer from 0 to 2, $n$ represents an integer from 0 to 3, Y represents halo and $R_1$ and $R_2$ independently represent hydrogen, lower alkyl, phenyl or substituted-phenyl, or, together with the nitrogen atom, form a heterocyclic ring also containing up to one oxygen atom in the heterocycle.

In the specification and claims, "lower alkyl" and "lower alkoxy" represent 1, to 2, to 3, to 4, carbon atom straight chain alkyl groups, such as, for example, methyl, ethyl, n-propyl or n-butyl, or a corresponding alkoxy group, respectively; the term "halo" with reference to R represents fluoro, chloro or bromo and with reference to Y represents chloro or bromo; and the term "substituted-phenyl" represents phenyl having lower alkyl, lower alkoxy, chloro or bromo substitution.

The compounds are useful as antimicrobial agents.

DESCRIPTION OF THE PREFERRED EMBODIMENTS

The compounds are prepared in the following several ways. To prepare a 1-arylthio-1,1-dihalomethanesulfonamide, a 1-(arylthio)methanesulfonamide is reacted with chlorine or bromine. The reaction is advantageously carried out in the presence of an appropriate organic solvent, i.e., methylene chloride or carbon tetrachloride as reaction medium. The reaction is carried out at a temperature at which hydrogen halide product of reaction is formed, advantageously at a temperature between about 20°C. and 40°C. The reaction consumes equimolar proportions of the starting materials and such proportions or a small excess of halogen are advantageously used. The reaction is carried out in the presence of pyridine as acid acceptor for the by-product hydrogen halide.

In carrying out the reaction, a solution of halogen in an inert organic solvent such as, for example, carbon tetrachloride, is added to the 1-arylthio-methanesulfonamide and the acid acceptor in an inert solvent, advantageously substantially equimolar proportions of the primary reactants, and the reaction mixture is stirred until the reaction is substantially complete. The progress of the reaction can be monitored by examining the nuclear magnetic resonance spectrum of the reaction mixture. The dihalomethanesulfonamide product in solution in the reaction medium is separated from by-product pyridine hydrohalide salt, the filtrate cooled and the dihalomethanesulfonamide product crystallized therefrom. If necessary, it is recrystallized from an appropriate solvent such as methanol, ethanol or the like.

The corresponding 1-(arylsulfinyl)methanesulfonamide or 1-(arysulfonyl)methanesulfonamide is halogenated with substantially two molar proportions of alkali metal hypohalite, advantageously formed in situ from halogen and aqueous alkali metal hydroxide. Such reaction is advantageously carried out by slurrying the 1-(arylsulfinyl)-or 1-(arylsulfonyl)methanesulfonamide in aqueous alkali metal hydroxide and adding thereto bromine or chlorine, advantageously with stirring and cooling and an ice bath to control the exotherm, then maintaining the reaction until halogenation is substantially complete. It is sometimes advantageous to have dioxane present as co-solvent. The solid product is filtered off and recrystallized, advantageously from methanol or ethanol, to give the corresponding arylsulfinyl-or arylsulfonyl-dihalomethanesulfonamide product.

The following examples additionally describe representative specific embodiments and the best modes contemplated by the inventors of carrying out the invention. Temperature is given in Centigrade degrees. The compounds are identified by elemental analysis and by nuclear magnetic resonance spectroscopy.

EXAMPLE 1

1,1-Dibromo-N,N-dimethyl-1-(phenylthio)methanesulfonamide

To a solution of 1.0 g. (4.32 mmol) of N,N-dimethyl-1-(phenylthio)methanesulfonamide and 1.683 g. of dry pyridine in 15 ml. of carbon tetrachloride was added a solution of 3.38 g. (21.2 mmol) of bromine in 15 ml. of carbon tetrachloride. After stirring for 19 hours, a yield of 80% of the titular product was obtained; m.p. 128°–129°C.

Anal. Calcd. for $C_9H_{11}Br_2NO_2S_2$: C, 27.78; H, 2.85; Br, 41.07; N, 3.60; S, 16.48 Found: C, 27.52; H, 2.81; Br, 40.6 ± 0.2; N, 3.65; S, 16.52.

EXAMPLE 2

1,1-Dibromo-N,N-dimethyl-1-(phenylsulfinyl)-methanesulfonamide

A slurry of 16.1 g. (65 mmol) of crude N,N-dimethyl-1-(phenylsulfinyl)methanesulfonamide (containing ca. 30% N,N-dimethyl-1-(phenylthio)methanesulfonamide as an impurity) in a solution of 8.0 g. (0.20 mol) of sodium hydroxide in 200 ml. of water was stirred and cooled in an ice bath. To this slurry, 32.0 g. (0.2 mol) of bromine was added and stirring continued for 18 hours. The solid which precipitated was filtered off, washed with water, and recrystallized from ethanol to give 13.5 g. (77% yield based on N,N-dimethyl-1-(phenylsulfinyl)methanesulfonamide) of the title compound as white platelets, m.p. 142°–143°C. (dec).

Anal. Calcd. for $C_9H_{11}Br_2NO_3S_2$: C, 26.68; H, 2.74; Br, 39.45; N, 3.46; S, 15.83. Found: C, 26.3.; H, 2.59; Br, 40.9 ± 0.2; N, 3.5; S, 15.43.

EXAMPLE 3

1,1-Dibromo-N,N-dimethyl-1-(phenylsulfonyl)-methanesulfonamide

A 150 ml. portion of a solution of 11 g. of sodium hydroxide in 250 ml. of water was added to 8.0 g. (0.304 mol) of N,N-dimethyl-1-(phenylsulfonyl)methtanesulfonamide. To the remainder of the sodium hydroxide solution was added 14.0 g. of bromide and this was added dropwise to the sulfone with stirring. The dibromosulfone product was filtered off after 30 minutes and recrystalized from ethanol to give 12.0 g. (84% yield) of product as white crystals; m.p. 144°–145°C.

Anal. Calcd. for $C_9H_{11}Br_2NO_4S_2$: C, 25.67; H, 2.63; S, 15.23; N, 3.33; Br, 37.95. Found: C, 26.12, 26.03; H, 2.73, 2.60; S, 15.19, 15.12; N, 3.68, 3.78.

EXAMPLE 4

1,1-Dibromo-1-((p-bromophenyl)sulfonyl)methanesulfonamide

A solution of 1.71 g. (6-06 mmol) of 1-((4-bromophenyl)thio)methanesulfonamide, 2 ml. of 30% aqueous hydrogen peroxide and 6 ml. of glacial acetic acid was heated to reflux for one hour and poured on ice. Filtration of the product gave 1.31 g. of crude sulfone (m.p. 162°–165°C.). This was dissolved in 50 ml. of aqueous 1% sodium hydroxide at 5°C. and 2 g. of bromine added. A tacky precipitate formed which solidified on trituration with chloroform and was recrystallized from $CHCl_3/CH_3OH$/hexane to give 0.82 g. of white crystals; m.p. 192°C.

Anal. Calcd. for $C_7H_6Br_3NO_4S_2$: Br, 50.79. Found: Br, 51.1 ± 0.8.

EXAMPLE 5

1,1-Dichloro-((p-methoxyphenyl)sulfonyl)-N,N-dimethylmethanesulfonamide

A 15 ml. portion of aqueous 5% sodium hypochlorite solution was added to a solution of 0.5 g. (1.7 mmol) of 1-((p-methoxyphenyl)sulfonyl)-N,N-dimethylmethanesulfonamide in 50 ml. of dioxane. After one hour, the reaction mixture was acidified with hydrochloric acid, and the dioxane removed in vacuo, leaving a white solid. The solid was slurried with water, filtered off, and recrystallized from absolute ethanol to give 0.37 g. of the title compound as white crystals, m.p. 145°–147°C.

Anal. Calcd. for $C_{10}H_{13}Cl_2NO_5S_2$: C, 33.15; H, 3.62; Cl, 19.58; N, 3.86; S, 17.70. Found: C, 33.20; H, 3.50; Cl, 19.70; N, 4.00; S. 17.90.

EXAMPLE 6

1-(Arylsulfonyl)-1,1-dichloromethanesulfonamides

Pursuant to the procedure of Example 5, the following compounds were prepared:

TABLE I 1-(Arylsulfonyl)-1,1-dichloromethanesulfonamides

| | $R_n$ | $NR_1R_2$ | m.p.,°C. | Calcd. C | H | Cl | N | S | Analyses Found C | H | Cl | N | S |
|---|---|---|---|---|---|---|---|---|---|---|---|---|---|
| a) | 4-$CH_3$ | $NH_2$ | 181–183 | 30.20 | 2.85 | 22.28 | 4.40 | 20.15 | 30.40 | 2.80 | 22.30 | 4.43 | 20.20 |
| b) | 4-Cl | morpholino | 163–165 | 32.32 | 2.96 | 26.03 | 3.43 | 15.69 | 32.30 | 2.99 | 25.90 | 3.52 | 15.90 |
| c) | H | 4-phenylpiperidino | 185–187 | 48.21 | 4.27 | 15.82 | 3.12 | 14.30 | 47.80 | 4.43 | * | 3.44 | 14.20 |
| d) | 3,4-$Cl_2$ | $NH_2$ | 125–128 | 22.54 | 1.35 | 38.03 | 3.75 | 17.17 | 22.50 | 1.46 | 38.00 | 3.72 | 17.20 |
| e) | 2,4,5-$Cl_3$ | $NH_2$ | 170–172 | 20.63 | 0.99 | 43.50 | 3.44 | 15.74 | 20.90 | 0.99 | * | 3.40 | 15.90 |

*Not determined

The compounds of the invention are employed as antimicrobials for the control of bacteria, fungi and yeasts. For such uses, the compounds can be employed in an unmodified form or dispersed on a finely divided solid and employed as dusts. Such mixtures can also be dispersed in water with the aid of a surface-active agent and the resulting emulsions employed as sprays. In other procedures, the products can be employed as active constituents in solvent solutions, oil-in-water or water-in-oil emulsions. The augmented compositions are adapted to be formulated as concentrates and subsequently diluted with additional liquid or solid adjuvants to produce the ultimate treating compositions. Good results are obtained when employing compositions containing antimicrobial concentrations and usually from about 25 to 10,000 parts by weight of one or more of the compounds per million parts of such compositions.

In representative operations, compounds of the present invention were tested for their activity as antimicrobials using conventional agar dilution tests. The following Table presents results, expressed as percent growth inhibition (numerator) over concentration of toxicant in parts per million (denominator).

TABLE II

| Example | Sa | Ca | Ec | Pa | St | Mp | Tm | Bs | Cp | Aa | Pp | At | Rn |
|---|---|---|---|---|---|---|---|---|---|---|---|---|---|
| 1 | 50/100 | | | | | 100/100 | 100/500 | 50/500 | | | 100/500 | 100/500 | |
| 2 | 100/100 | 100/100 | 100/100 | 100/100 | 100/100 | 100/100 | 100/100 | 100/100 | 100/100 | 100/100 | 100/100 | 100/100 | 100/100 |
| 3 | 100/100 | 100/100 | 100/100 | 100/100 | 100/100 | 100/100 | 100/100 | 100/100 | 100/100 | 100/100 | 100/100 | 100/100 | 100/100 |
| | 500/100 | 100/100 | 100/100 | 100/100 | 100/100 | 100/100 | 100/100 | 100/100 | 100/100 | 100/100 | 100/100 | 100/100 | 100/100 |

TABLE II -continued

| Example | Sa | Ca | Ec | Pa | St | Mp | Tm | Bs | Cp | Aa | Pp | At | Rn |
|---|---|---|---|---|---|---|---|---|---|---|---|---|---|
| 4 | 100 | 100 | 100 | 100 | 100 | 100 | 100 | 100 | 100 | 100 | 100 | 100 | 100 |
|   | 500 | 500 | 500 | 500 | 500 | 500 | 100 | 100 | 500 | 500 | 100 | 500 | 500 |
| 6a | 100 |  |  |  | 50 | 100 | 100 | 100 |  |  | 50 |  |  |
|   | 500 |  |  |  | 500 | 500 | 500 | 100 |  |  | 500 |  |  |
| 6b |  |  |  |  |  | 100 | 100 | 100 | 50 |  |  |  |  |
|   |  |  |  |  |  | 10 | 10 | 10 | 100 |  |  |  |  |
| 6c |  |  |  |  |  | 50 |  |  |  |  |  |  |  |
|   |  |  |  |  |  | 500 |  |  |  |  |  |  |  |
| 6d | 100 | 100 |  |  | 50 | 100 | 100 | 100 | 50 |  | 100 |  |  |
|   | 100 | 500 |  |  | 500 | 10 | 100 | 10 | 500 |  | 100 |  |  |
| 6e | 100 | 100 |  |  | 50 | 100 | 100 | 100 | 100 |  | 100 |  |  |
|   | 100 | 500 |  |  | 500 | 10 | 10 | 10 | 500 |  | 100 |  |  |

Sa = S. aureus     Ca = C. albicans     Ec = E. coli     Pa = P. aeruginosa
St = S. typhosa     Mp = M. phlei     Tm = T. mentagrophytes
Bs = B. subtilis     Cp = C. pelliculosa     Aa = A. aerogenes     Pp = P. pullulans
At = A. terreus     Rn = R. nigricans The process for making the starting materials herein which are 1-(arylsulfinyl)methanesulfonamides and 1-(arylsulfonyl)methanesulfonamides, is described in U.S. Pat. No. 3,862,184, filed Mar. 5, 1973. The process for making 1-(arylthio)methanesulfonamides is described in our copending U.S. Pat. application Ser. No. 314,793, filed Dec. 13, 1972.

What is claimed is:

1. A compound represented by the formula

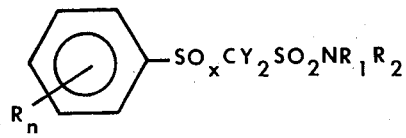

wherein R represents lower alkyl, lower alkoxy, fluoro, chloro or bromo, $x$ represents an integer from 0 to 2, $n$ represents an integer from 0 to 3, Y represents chloro or bromo and $R_1$ and $R_2$ independently represent hydrogen, lower alkyl, or, together with the nitrogen atom, form a morpholinyl, piperidinyl or phenylpiperidinyl heterocyclic ring.

2. The compound of claim 1 which is 1,1-dibromo-N,N-dimethyl-1-(phenylthio)methanesulfonamide.

3. The compound of claim 1 which is 1,1-dibromo-N,N-dimethyl-1-(phenylsulfinyl)methanesulfonamide.

4. The compound of claim 1 which is 1,1-dibromo-N,N-dimethyl-1-(phenylsulfonyl)methanesulfonamide.

5. The compound of claim 1 which is 1,1-dibromo-1-((p-bromophenyl)sulfonyl)methanesulfonamide.

6. The compound of claim 1 which is 1,1-dichloro-1-((p-methoxyphenyl)sulfonyl)-N,N-dimethylmethane sulfonamide.

7. The compound of claim 1 which is 1,1-dichloro-1-(p-tolylsulfonyl)methanesulfonamide.

8. The compound of claim 1 which is 4-((dichloro((4-chlorophenyl)sulfonyl)methyl)sulfonyl)-morpholine.

9. The compound of claim 1 which is 1-((dichloro(phenylsulfonyl)methyl)sulfonyl)-4-phenylpiperidine.

10. The compound of claim 1 which is 1,1-dichloro-1-((3,4-dichlorophenyl)sulfonyl)methanesulfonamide.

11. The compound of claim 1 which is 1,1-dichloro-1-((2,4,5-trichlorophenyl)sulfonyl)methanesulfonamide.

* * * * *